US007857780B2

(12) United States Patent
Sommers et al.

(10) Patent No.: US 7,857,780 B2
(45) Date of Patent: Dec. 28, 2010

(54) DISCRETELY ADJUSTABLE ORTHOPEDIC TRACTION USING CONSTANT-FORCE SPRINGS

(75) Inventors: Mark B. Sommers, Beaverton, OR (US); William B. Geissler, Brandon, MS (US)

(73) Assignee: Acumed LLC, Hillsboro, OR (US)

( * ) Notice: Subject to any disclaimer, the term of this patent is extended or adjusted under 35 U.S.C. 154(b) by 277 days.

(21) Appl. No.: 12/211,719

(22) Filed: Sep. 16, 2008

(65) Prior Publication Data

US 2010/0069809 A1     Mar. 18, 2010

(51) Int. Cl.
*A61F 5/00*     (2006.01)
(52) U.S. Cl. .............................. 602/36; 602/16; 602/20
(58) Field of Classification Search ................... 602/16, 602/20, 21–22, 32–36; 5/621, 623; 128/878–879
See application file for complete search history.

(56) References Cited

U.S. PATENT DOCUMENTS

| 2,997,250 | A | * | 8/1961 | Collins | 242/375.1 |
| 3,683,900 | A | * | 8/1972 | Alessi et al. | 602/32 |
| 4,445,506 | A | * | 5/1984 | Johansson et al. | 602/39 |
| 5,735,806 | A | * | 4/1998 | Leibovic | 602/32 |
| 6,811,541 | B2 | * | 11/2004 | Lambert | 602/36 |
| 7,771,378 | B2 | * | 8/2010 | Price et al. | 602/36 |

* cited by examiner

*Primary Examiner*—Michael A. Brown
(74) *Attorney, Agent, or Firm*—Kolisch Hartwell, PC

(57) ABSTRACT

System, including method and apparatus, for applying traction to a patient's limb using constant-force springs. The constant-force springs may include one or more main springs that apply a base tractive force and at least one supplementary spring that can apply a supplementary tractive force to the limb. The at least one supplementary spring may be changeable reversibly between uncoupled and coupled configurations while the base tractive force is applied continuously to the limb and without repositioning the limb, thereby providing discrete adjustment of traction force while the limb remains in traction.

20 Claims, 3 Drawing Sheets

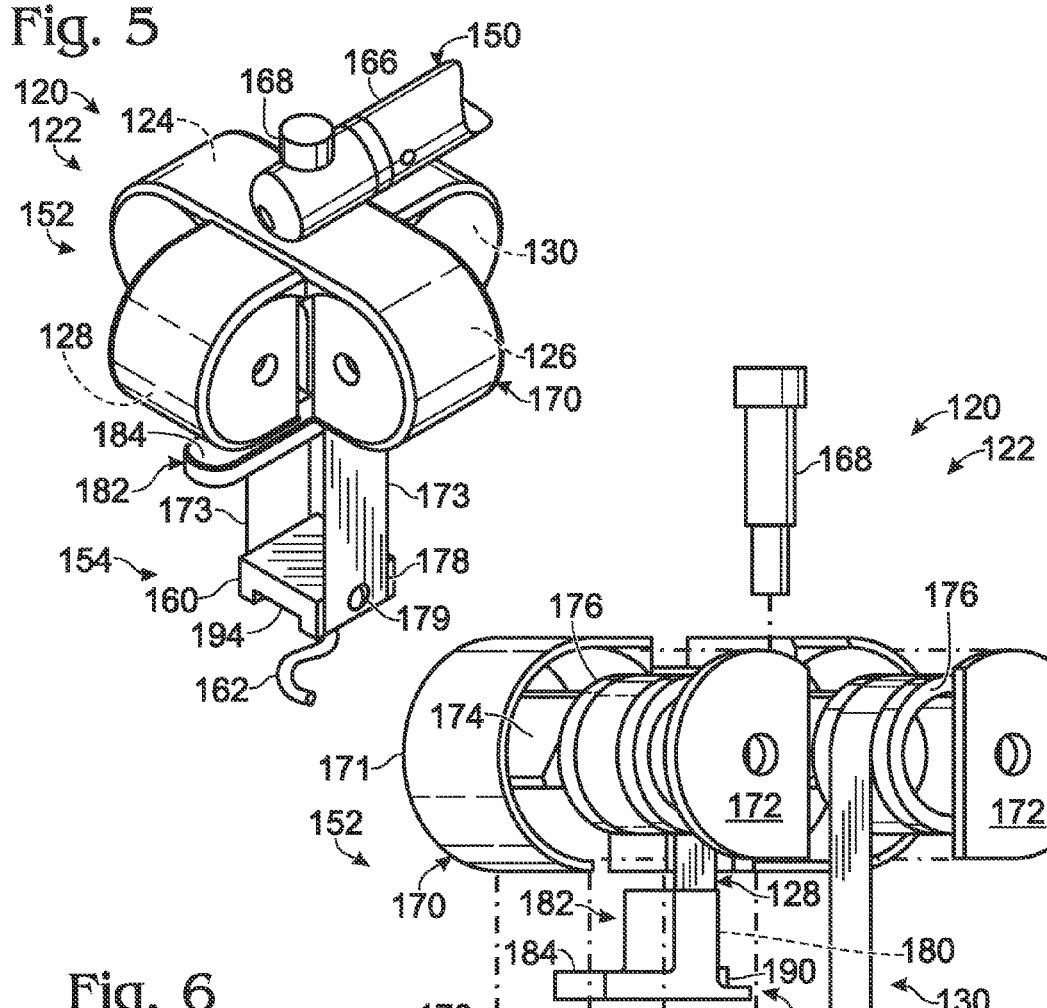
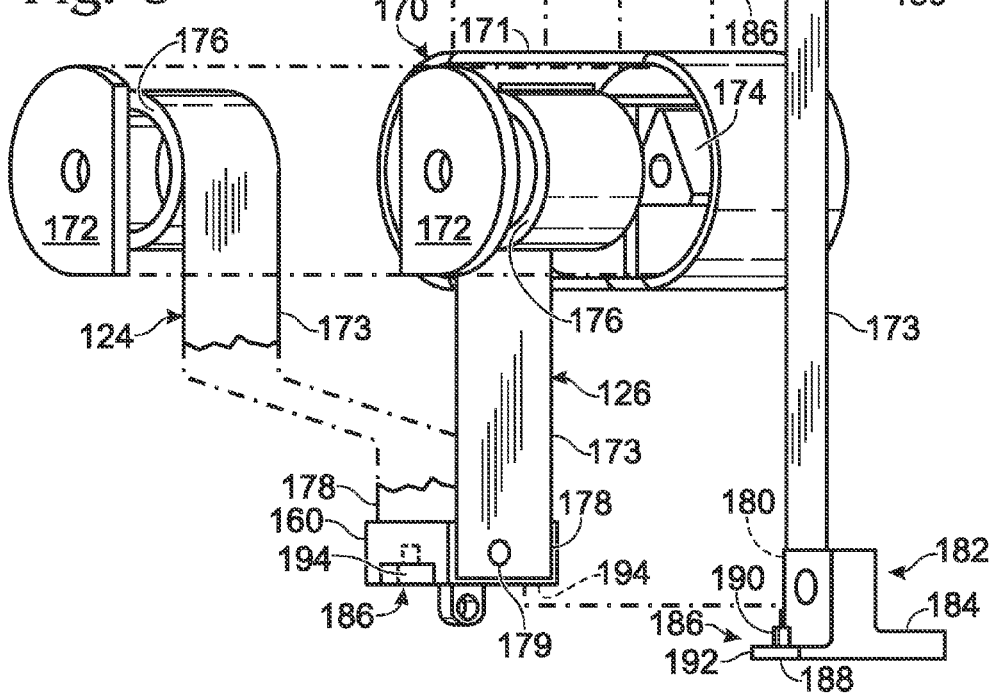

DISCRETELY ADJUSTABLE ORTHOPEDIC TRACTION USING CONSTANT-FORCE SPRINGS

Joint surgery on a patient's limb frequently involves application of traction to the limb. For example, traction can be used to distract the bones of a limb joint (such as the wrist, ankle, elbow, knee, shoulder, or hip) during open or arthroscopic surgery, to facilitate access of surgical tools or arthroscopic instruments.

Tractive forces frequently are applied during arthroscopic surgery on a limb with the aid of a traction device that utilizes continuously adjustable traction, to offer a continuous range of tractive forces. The availability of a range of tractive forces is generally considered to be important because a surgeon can select the desired tractive force suitable for each individual patient and surgical procedure. Also, continuously adjustable traction allows the surgeon to readjust the applied tractive force as needed during a surgical procedure.

However, a traction device with continuously adjustable traction may not be capable of maintaining a constant tractive force on a patient's limb during the course of a surgical procedure. For example, the tractive force on the limb decreases as the limb gradually stretches under traction or if there is any gradual or sudden slippage of the limb relative to the traction device. Also, if the traction device permits the limb to be moved with respect to the traction device while under traction, the tractive force on the limb may increase or decrease with distinct positions of the limb. Accordingly, the traction device may require repeated readjustment to maintain a generally constant tractive force during a surgical procedure, which may prolong surgery, thereby increasing cost and risk.

Constant-force springs have been introduced into orthopedic traction devices to apply a constant force to a patient's body, such as to a patient's spine for therapeutic purposes. However, these constant-force devices are not suitable for applying traction to a limb during surgery because they are not sufficiently adjustable. Improved traction devices for use during surgery on a limb are needed.

SUMMARY

The present disclosure provides a system, including method and apparatus, for applying traction to a patient's limb using constant-force springs. The constant-force springs may include one or more main springs that apply a base tractive force and at least one supplementary spring that can apply a supplementary tractive force to the limb. The at least one supplementary spring may be changeable reversibly between uncoupled and coupled configurations while the base tractive force is applied continuously to the limb and without repositioning the limb, thereby providing discrete adjustment of traction force while the limb remains in traction.

BRIEF DESCRIPTION OF THE DRAWINGS

FIG. 5 is a fragmentary view of the traction system of FIG. 4 taken generally around a spring assembly that includes the constant-force springs.

FIG. 6 is an exploded view of the spring assembly of FIG. 5, taken as in FIG. 5 but with one of the two supplementary springs in an extended configuration, in accordance with aspects of the present disclosure.

DETAILED DESCRIPTION

Figure 1:
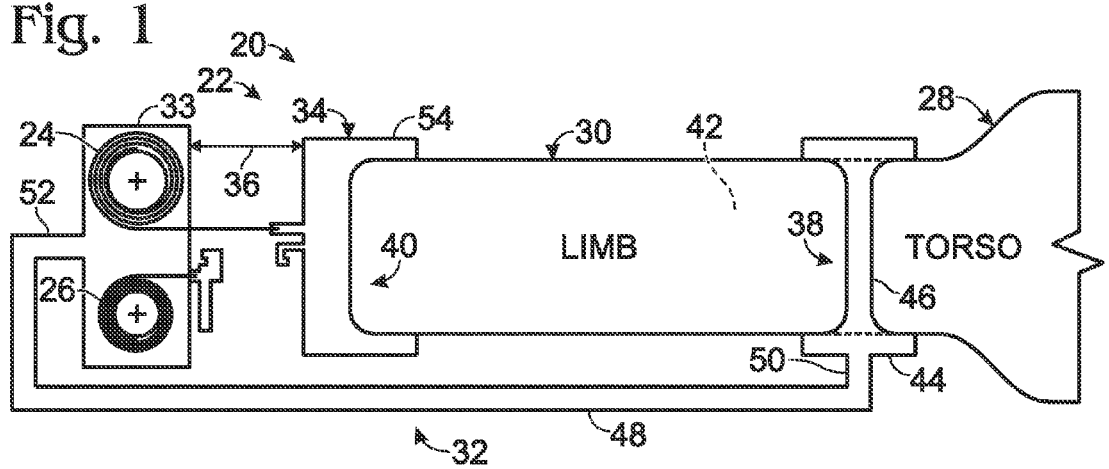
FIG. 1 is a schematic view of an exemplary traction system including a plurality of constant-force springs, with a main spring applying a constant, base tractive force to a patient's limb while a supplementary spring is in an uncoupled configuration that does not apply traction, in accordance with aspects of the present disclosure.

The present disclosure provides a system, including method and apparatus, for applying discretely adjustable traction to a patient's limb.

The system may include an orthopedic traction apparatus that attaches to a patient's limb. The traction apparatus may include a plurality of constant-force springs supported rotatably by the traction apparatus such that each spring is extendable by unwinding. The plurality of constant-force springs may include one or more main springs operatively disposed to apply a base tractive force to the limb. The plurality of constant-force springs also may include at least one supplementary spring that is changeable between an uncoupled configuration (a storage/retracted configuration) that is not operatively disposed to apply a supplementary tractive force to the limb and a coupled configuration (an extended/deployed configuration) that is operatively disposed to apply the supplementary tractive force to the limb. The at least one supplementary spring may be changeable reversibly between the uncoupled and coupled configurations while the base tractive force is applied continuously to the limb and/or without repositioning the limb, thereby providing discrete adjustment of traction force while the limb remains in traction.

In some embodiments, a leading end of the at least one supplementary spring may be connected to a handle and to at least a portion of a fastener mechanism. The handle may be configured to be manipulated to extend the supplementary spring, such as independently of the main springs, and to actuate the fastener mechanism such that the supplementary spring is placed in the coupled configuration.

The present disclosure provides a method of applying traction to a patient's limb using a traction apparatus. The traction apparatus may include a plurality of constant-force springs supported rotatably by the traction apparatus such that each spring is extendable by unwinding. The constant-force springs may include one or more main springs operatively disposed to apply a base tractive force to a limb and at least one supplementary spring that is changeable between an uncoupled configuration in which the supplementary spring is not operatively disposed to apply a supplementary tractive force to the limb and a coupled configuration in which the supplementary spring is operatively disposed to apply the supplementary tractive force. The traction apparatus may be attached to a patient's limb. The at least one supplementary spring may be extended independently of the main springs by pulling a handle attached to a leading end of the supplementary spring. The supplementary spring may be placed reversibly in the coupled configuration from the uncoupled configuration at any time, whether or not the main springs are extended. The base tractive force and the supplementary tractive force may be applied together to the limb.

The system of the present disclosure offers substantial advantages for use during surgery on a limb (e.g., conventional and/or arthroscopic limb surgery, among others). The system provides adjustable application of a predetermined set of discrete, constant tractive forces, each of which may be selected before and/or during limb surgery and/or limb traction according to the needs of the patient and/or the preference of the surgeon. Each discrete tractive force may be applied quickly, easily, and reproducibly, and remains constant. Accordingly, the system may permit application of the same tractive force (1) as a limb pivots, stretches, or slips, (2) with the same limb during separate surgical procedures, (3) and/or with limbs of different size.

I. Exemplary Traction System

FIG. 1 shows a schematic representation of an exemplary traction system 20 including a traction apparatus 22 that incorporates a plurality of constant-force springs 24, 26. The traction apparatus may be discretely adjustable to apply distinct constant tractive forces to a patient's body 28 and particularly a limb 30 thereof (i.e., an arm, a leg, or any portion of an arm or leg) using corresponding distinct combinations of the constant-force springs.

Traction apparatus 22 may incorporate a frame 32 that includes a support member 33, and also may incorporate a carriage assembly 34 (also termed a limb securement assembly) coupled movably to the frame by one or more of the constant-force springs. More particularly, carriage assembly 34 may be coupled to the frame such that the carriage assembly can move toward and away from support member 33, to change a separation 36 (also termed a separation distance) between the carriage assembly and the support member. The one or more constant-force springs that couple the frame to the carriage assembly may apply a constant tractive force to the limb over a continuous range of separation 36. In other words, traction apparatus 22 may be self-adjusting to provide continuous application of the same tractive force as limb 30 slips, stretches, or is deliberately reoriented with respect to at least a portion of the frame (e.g., a base thereof).

Frame 32 may be configured to span (also termed bridge) any suitable portion (or all) of limb 30 to which the tractive force is applied. For example, frame 32 may be configured to extend generally at least from a first region 38 to a second region 40 of limb 30 (and/or the torso) and may span at least one joint 42 of the limb, to distract bones of the joint. First region 38 may be disposed more proximally along the limb (and/or may be part of the torso) and second region 40 may be disposed more distally along the limb, or vice versa. In some examples, the second region may be a distal end, a distal region, and/or a proximal region of an arm or a leg, and the first region may be provided by a forearm, an upper arm, a lower leg, an upper leg, the torso, or a combination thereof. Exemplary joints that may be spanned include a joint of the shoulder, elbow, wrist, hand, fingers, or any suitable combination thereof; or a joint of the hip, knee, ankle, foot, toes, or any suitable combination thereof.

The frame may be configured to be received by and/or secured to first region 38 of the limb. Accordingly, the frame may, for example, include a base 44 that receives and engages first region 38 and/or may include a first securement member 46 that attaches the first region of the limb to the frame, such as to the base of the frame.

The frame also may include a bridge component 48, which may extend generally from base 44 and/or first securement member 46, past second region 40, to an opposing end of the frame. The bridge component may be supported by base 44. The bridge component may have opposing first and second ends 50, 52. First end 50 may be connected to base 44, such as connected fixedly and/or pivotably, and second end 52 may be coupled to carriage assembly 34 using one or more of constant-force springs 24, 26.

Carriage assembly 34 may provide a connection between constant-force springs 24, 26 and second region 40 of limb 30. For example, the carriage assembly may include at least one second securement member 54 that engages and attaches to second region 40 of limb 30. Exemplary first and second securement members that may be suitable include finger traps, toe traps, straps, harnesses, clamps, braces, or the like.

Figure 2:
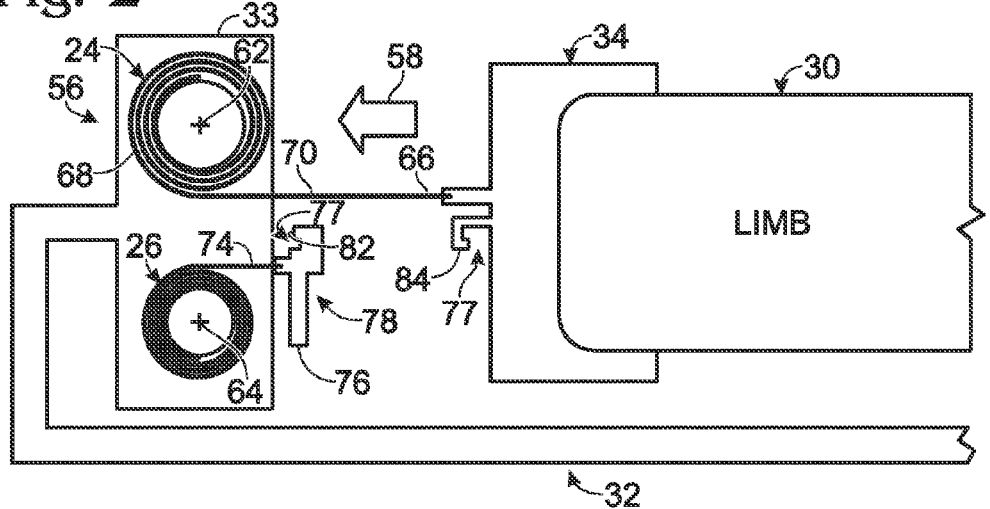
FIG. 2 is a fragmentary view of the traction system of FIG. 1.

FIG. 2 shows selected aspects of traction system 20, particularly a spring assembly 56 exerting a base tractive force 58 on limb 30. The spring assembly may include at least one support member 60 that rotatably supports the constant-force springs 24, 26 for rotation about respective rotation axes 62, 64. Support member 60 for a constant-force spring may be included in frame 32, as shown here, such that the constant-force spring is supported rotatably by the frame, or may be included in carriage assembly 34, such that the constant-force spring is supported rotatably by the carriage assembly. Accordingly, a leading end of each constant-force spring may be attached (or couplable) to carriage assembly 34, as shown here for a leading end 66 of spring 24. Alternatively, the orientation of any subset (or all) of the springs may be reversed, with at least one of the springs supported rotatably by carriage assembly 34 and its leading end attached (or couplable) to frame 32.

Each constant-force spring may be constructed as a coil of resilient material, such as a coiled (rolled) ribbon. With the spring rotatably supported, a coiled section 68 of the spring may rotate about a rotation axis (e.g., axis 62) as an extended section 70 of increasing (or decreasing) length unwinds from (or winds onto) coiled section 68. The spring may be biased toward its fully coiled configuration but the recoiling force may be generated predominantly near coiled section 68 in extended section 70. Accordingly, the spring applies a constant force, such as base tractive force 58, on a leading end of the constant-force spring over a continuous range of lengths of extended section 70.

The rotation axes about which the constant-force springs rotate to extend and retract may have any suitable relative relationship. For example, at least two or all of the rotation axes may be parallel to one another, such as with the constant-force springs arranged generally along a line. Alternatively, or in addition, at least two of the rotation axes may be transverse to each other, such as at least substantially orthogonal to one another. Accordingly, the constant-force springs may include at least three springs disposed on at least three sides of an axis, such as four springs in a generally axisymmetric relationship. In some embodiments, the constant-force springs may include a first pair of springs arranged transversely or at least substantially orthogonally to a second pair of springs. Arrangement of constant-force springs around an axis may be advantageous in some cases to balance the forces exerted on a carriage assembly by the springs.

Base tractive force 58 may be applied by one or more main springs 24. For example, the base tractive force may be applied by only one main spring 24, as shown in FIG. 2, or may be applied by two or more main springs. The two or more main springs may couple frame 32 to carriage assembly 34 in parallel such that the tractive forces exerted by the main springs are added together. With two or more main springs, the main springs each may exert about the same magnitude of tractive force or may exert tractive forces of different magnitude.

Figure 3:
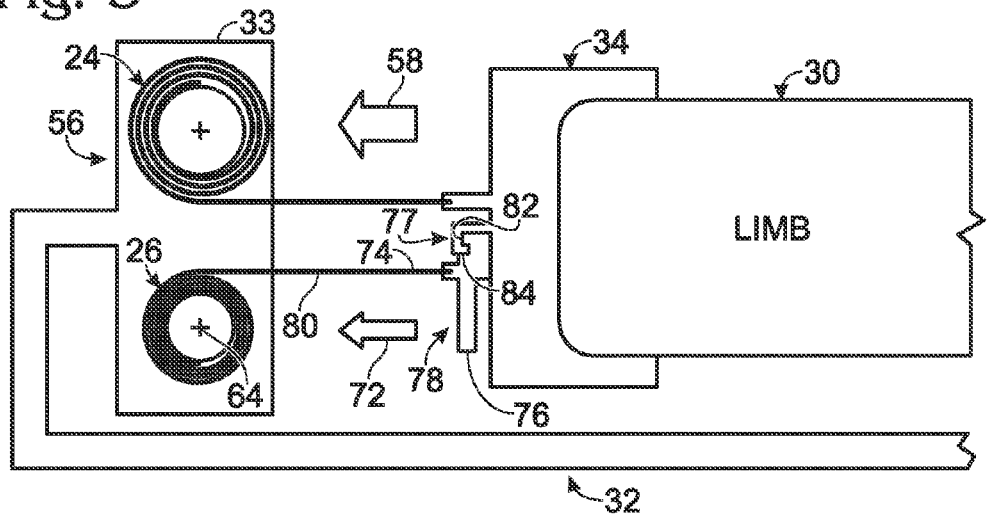
FIG. 3 is a fragmentary view of the traction system of FIG. 1 taken generally as in FIG. 2 but with the supplementary spring in a coupled configuration such that the base tractive force applied to the limb is incremented by a constant, supplementary tractive force applied by the supplementary spring, in accordance with aspects of the present disclosure.

FIGS. 2 and 3 illustrate how spring assembly 56 may be adjusted to provide a discrete increase or decrease in the tractive force applied to limb 30. Spring assembly 56 includes at least one supplementary spring 26 configured to apply at least one supplementary tractive force 72 to limb 30 (see FIG. 3). Each supplementary spring 26 may be changeable between an uncoupled configuration (also termed a retracted or storage configuration)(e.g., FIG. 2), in which the supplementary spring is not operatively disposed and supplementary tractive force 72 is not applied, and a coupled configuration (also termed an extended or deployed configuration) (e.g., FIG. 3), in which the supplementary spring is operatively disposed and supplementary tractive force 72 is applied to the limb. By placing supplementary spring 26 in the coupled configuration, supplementary spring 26 may couple frame 32 to carriage assembly 34 in parallel with main spring 24, to increase the tractive force applied to the limb a discrete amount (i.e., by the supplementary tractive force). In contrast, by placing supplementary spring 26 in the uncoupled configuration from the coupled configuration, the tractive force on the limb is reduced a discrete amount (i.e., by the supplementary tractive force). Each supplementary spring may be changeable between coupled and uncoupled configurations independent of the operative disposition of the main springs. In the coupled configuration, a leading end 74 of the supplementary spring may be attached to carriage assembly 34 (or to frame 32 if the orientation of the supplementary spring is reversed).

Supplementary spring 26 may be changeable between the uncoupled configuration and the coupled configuration using a handle 76 and a fastener mechanism 77. Both handle 76 and at least a portion of fastener mechanism 77 may be connected to leading end 74 of the supplementary spring. The portion of the fastener mechanism may be discrete from the supplementary spring, such with a handle member 78 that provides handle 76 and the portion of fastener mechanism 77. Alternatively, the portion of the fastener mechanism may be connected integrally to the supplementary spring. For example, the fastener mechanism may include a hole defined by the supplementary spring and configured to be received on a pin or a hook provided by the carriage assembly. In any event, handle 76 may be grasped and manipulated, generally by pulling on the handle, to extend supplementary spring 26 from its retracted/storage configuration. The supplementary spring may be extended independently of the main springs. The supplementary spring may be extended a suitable amount to increase the length of a leading section 80 of spring 26 until fastener mechanism 77 can be actuated. Actuation of the fastener mechanism may be achieved by further manipulation of handle 76 to attach leading end 74 to carriage assembly 34 (or to frame 32 if the orientation of the supplementary spring is reversed), thereby producing the coupled configuration and incrementing the tractive force applied to the limb.

Fastener mechanism 77 may, for example, be formed by mating structures 82, 84 connected respectively to leading end 74 and to carriage assembly 34 (or to frame 32 if the orientation of the supplementary spring is reversed). The mating structures may be generally complementary, such as a pin and a cavity, a hook and an eyelet, or the like. Fastener mechanism 77 may be described as a quick-release fastener mechanism, which may be actuated and uncoupled by manipulation of handle 76 (i.e., by hand). Furthermore, the leading end(s) of the one or more main springs may be attached to the frame or to the carriage assembly more permanently than the leading end of the at least one supplementary spring in the coupled configuration. A more permanent attachment of the main spring(s) relative to the least one supplementary spring means that more time/effort and/or at least one tool is needed to uncouple the leading end(s) of the main spring(s).

The constant-force springs may include any suitable number and size of supplementary springs. If two or more supplementary springs are incorporated into a traction apparatus, the supplementary springs may be about the same size, to each exert about the same magnitude of tractive force, or may be distinct sizes to exert tractive forces of different magnitude. Each supplementary spring may apply a supplementary tractive force that is less than the base tractive force, for example, no more than about one-half of the base tractive force.

Traction system 20, and components thereof, may be manufactured from any suitable material(s), including, but not limited to, stainless steel, titanium or titanium alloy, cobalt chromium, aluminum alloys, and/or plastic, among others, including a combination thereof. These materials may be selected and/or finished to satisfy any suitable criteria, including strength, durability, appearance, and ease of use. For example, lighter-weight components may be selected to facilitate transportation and use of the traction system, while other more heavier components may be selected to provide increased stability, and heat and/or moisture-resistant materials may be selected to permit sterilization of one or more components of the traction system, among others.

II. Exemplary Traction System for the Forearm

Figure 4:
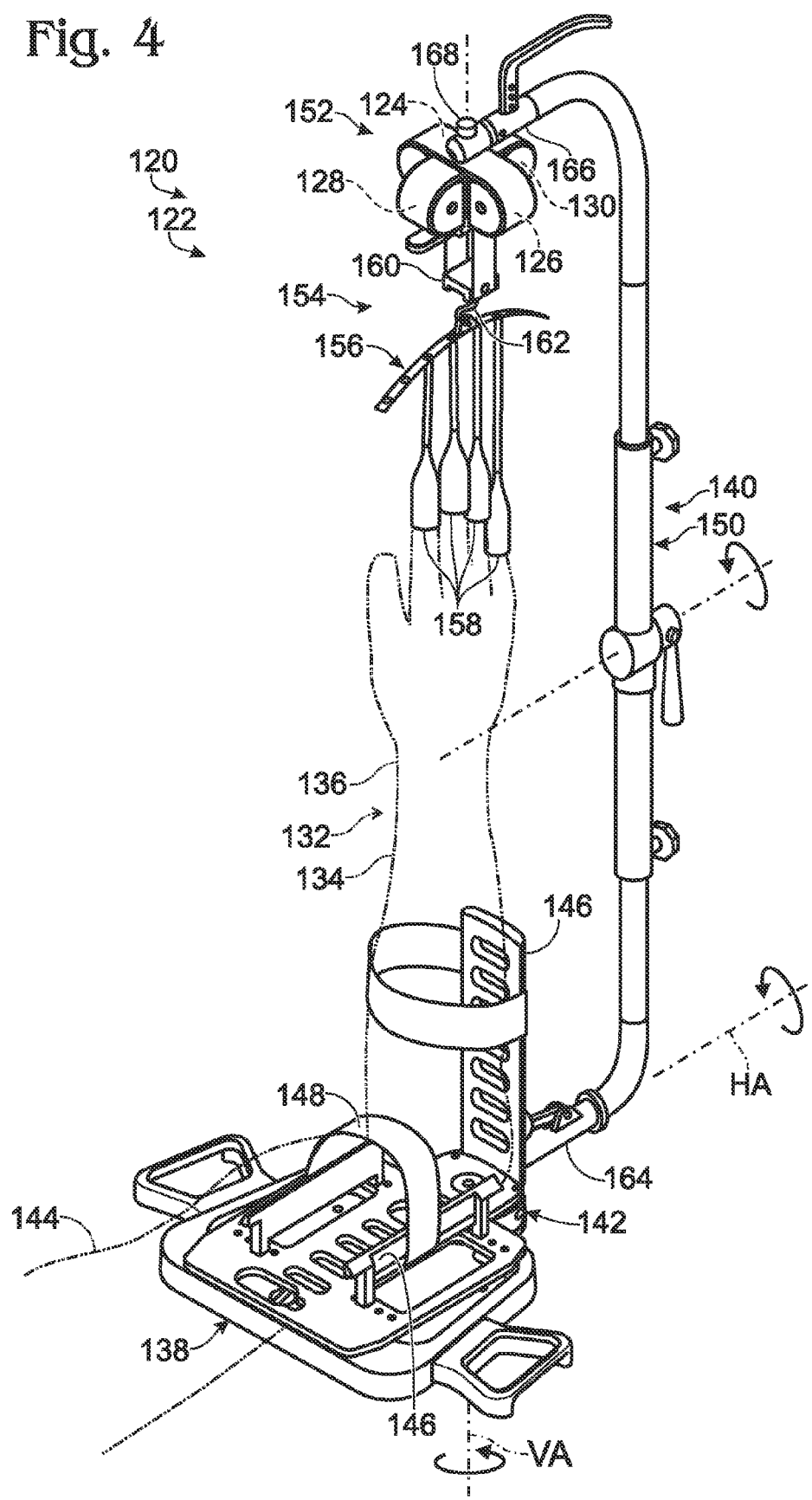
FIG. 4 is a view of another exemplary traction system that includes a plurality of constant-force springs, namely, two main springs and two supplementary springs, with a spanning member of the traction system in a vertical configuration applying vertical traction to a human forearm using a subset of the constant-force springs, in accordance with aspects of the present disclosure.

FIG. 4 shows another exemplary traction system 120 that includes a traction apparatus 122 incorporating a plurality of constant-force springs 124-130. Traction system 120 may be used to apply a constant tractive force, which is adjustable by discrete amounts, to a patient's limb 132, such as a forearm 134 and/or wrist 136 thereof, using the constant-force springs. Traction system 120 may include a base 138 connected pivotably to a spanning member 140 (also termed a tower arm) by a joint 142. However, any of the elements, features, and/or aspects disclosed below for traction system 120 and above for traction system 20 (e.g., see FIGS. 1-3) may be combined.

Base 138 may be configured to support the spanning member, the joint, and/or other components of the system, and to receive and hold at least a portion of a patient's limb. For example, FIG. 4 shows the base holding a distal end of a patient's upper arm 144 and a proximal end of forearm 134. The base may include one or more stops or fences 146 that restrict horizontal motion of a portion of the limb, and at least one securement member 148, such as a strap, that secures the portion of the limb to the base.

Spanning member 140 may be configured to apply a tractive force to at least a portion of a patient's limb using springs 124-130, and to determine the angular orientation of the patient's limb adjustably during use of the traction system. The spanning member may pivot about at least one axis using joint 142. For example, joint 142 may be configured to allow spanning member 140 to pivot about a vertical axis VA, a horizontal axis HA, or both VA and HA. VA and HA may be substantially orthogonal to each other. Furthermore, pivotal movement about VA and HA may be substantially independent or may be coupled. Pivotal adjustment of the spanning member relative to the base may facilitate instrument access and/or application of variable forms of traction to the patient's limb. In addition, pivotal adjustment of the spanning member relative to the base may be performed to reposition the patient's forearm while a constant tractive force is applied continuously to the forearm.

Spanning member 140 may include a bridge component 150 connected to and supporting a spring assembly 152 (with springs 124-130), which in turn may be coupled to a carriage assembly 154 (also termed a limb securement assembly). Carriage assembly 154 may be configured to attach to a distal end of patient's limb 132 and thus may include at least one securement member, such as a finger trap assembly 156 including finger traps 158. Carriage assembly 154 also may include a linkage member 160 and an S-hook 162 that connect springs 124-130 to finger trap assembly 156.

Bridge component 150 may include opposing first and second ends 164, 166. The first end of the bridge component may be pivotably connected to base 138 by joint 142, and the second end of the bridge component may be connected to spring assembly 152 (e.g., by a bolt 168), such that springs 124-130 are connected the second end of the bridge component. The bridge component may have an adjustable length and/or shape.

FIGS. 5 and 6 show respective assembled and exploded views of traction system 120 taken generally around spring assembly 152. In FIG. 5, both supplementary springs 128, 130 are in a storage (uncoupled) configuration, while in FIG. 6, supplementary spring 130 is in an extended configuration. The spring assembly may include a support member 170 (e.g., a housing) holding main springs 124, 126 and supplementary springs 128, 130. The support member may (or may not) at least substantially enclose springs 124-130. For example, the springs may be enclosed by housing body members 171 assembled with covers 172 that are secured to the body members with fasteners (see FIG. 6).

Each of springs 124-130 may be coupled rotatably to support member 170 such that a leading section 173 of each spring can be extended and then retracted with respect to the support member. A coiled trailing section of each spring may rotate about a respective axle 174 as the spring is extended and retracted. The spring may contact the axle or may be spaced from the axle by a bearing, which may reduce friction, thereby reducing any lag in application of tractive force as the spring is extended/retracted. Any suitable bearing may be used to reduce friction between the spring and the axle. Exemplary bearings that may be suitable include ball bearings, needle roller bearings, bushings, or a combination thereof, among others. In the present illustration, each spring is coiled (rolled) onto a respective spool 176 (also termed a bushing) that revolves on respective axle 174. A trailing end of each spring optionally may be secured to its respective spool to restrict the ability to completely unspool the spring and uncouple it from the support member.

Main springs 124,126 may be attached more permanently to at least a portion of carriage assembly 154 than supplementary springs 128, 130. For example, a leading end 178 of each main spring may be secured to linkage member 160 by a relatively more permanent fastener 179, such as a screw or a rivet. Accordingly, the main springs generally remain attached to linkage member 160 during normal use and storage of the traction apparatus.

Supplementary springs 128, 130 may be manually coupled to and uncoupled from linkage member 160 of carriage assembly 154 during use of the traction apparatus. A leading end 180 of each supplementary spring 128, 130 may be connected to a respective handle component 182. The handle component may engage support member 170 in the storage/retracted configuration of its connected supplementary spring, to prevent the supplementary spring from becoming fully coiled. The handle component may include a handle 184, which may, for example, be sized and shaped to be engaged between thumb and finger(s). The handle component also may include a portion of a fastener mechanism 186 that allows the supplementary spring to be coupled to linkage member 160 of carriage assembly 154. For example, handle component 182 may form a projection 188, such as a pin 190 extending from a tab 192, and linkage member 160 may define a cavity 194 shaped to receive projection 188 (e.g., to receive pin 190, tab 192, or both the pin and the tab). In other embodiments, the handle component (or the supplementary spring) may define a cavity (or a hole) configured to receive a projection formed by the linkage member. In any event, each handle component 182 may be manipulated to extend a supplementary spring from spring assembly 152 and to couple the supplementary spring to linkage member 160.

Main springs 124, 126 and supplementary springs 128, 130 may exert any suitable amounts of force. For example, the main springs may apply a relatively larger tractive force, and the supplementary springs each may apply a relatively smaller tractive force. In exemplary embodiments, for the purpose of illustration only, main springs 124, 126 each may exert six pounds of force and supplementary springs 128, 130 each may exert four pounds of tractive force, to permit adjustment among 12, 16, and 20 pounds of tractive force.

Further elements, aspects, and features that may be included in traction apparatus 120 are described in U.S. Patent No. 7,131,955, which is incorporated herein by reference.

III. Exemplary Methods of Applying Traction

The present disclosure provides a method of applying discretely adjustable traction to a patient's limb using constant-force springs. The method may be performed with any suitable combination and order of the steps presented in the remainder of this section and elsewhere in the present disclosure.

A first region of a patient's limb may be attached to a frame of a traction apparatus. The frame may include a base and a bridge component connected to the base. The bridge component may extend generally past a second region of the patient's limb. The first and second regions of the limb may be disposed generally longitudinally along the limb. The first region of the patient's limb may be received on and attached to the base.

The frame may be adjusted in shape and/or size before or during application of a tractive force to the limb. The shape of the frame may, for example, be adjusted by pivoting the bridge component with respect to the base, and then fixing the pivotal position of the bridge component. Alternatively, or in addition, the shape of the bridge component may be adjusted along its length, such as by pivoting a more proximal section of the bridge component relative to a more distal section of the bridge component and then fixing the pivotal position of the proximal section with respect to distal section. The length of the frame and/or the bridge component may be changed according to the type and/or size of the patient's limb, and/or according to the spacing between the first and second regions of the patient's limb to which a tractive force is to be applied. However, the ability of constant-force springs to apply a constant-force over a continuous range of extension of the springs, may reduce or eliminate the need to adjust the size of the frame to accommodate the individual limb size of each patient.

A second region of the patient's limb may be attached to at least a portion of a carriage assembly that is movable with respect to the frame. The carriage assembly may include at least one securement member that engages the second region of the limb when installed. In some embodiments, the carriage assembly also may include a linkage member that couples to and uncouples from the securement member. The linkage member may be attached to at least a subset of the constant-force springs before or after the linkage member is coupled to the securement member. In some cases, the linkage member and its attached constant-force springs may be coupled to the securement member after the securement member is installed on the limb. Accordingly, coupling of the linkage member to the securement member may be performed after one or more supplementary springs have been selected for use and attached to the linkage member.

A base tractive force may be applied to the patient's limb using one or more main springs of the constant-force springs. Application of the base tractive force may, for example, be realized by coupling the linkage member to the installed securement member, such as by forming a hooked connection between the linkage member and the securement member. Alternatively, application of the base tractive force may be realized by attachment of the securement member to the limb, with the securement member already coupled to at least a subset of the constant-force springs (i.e., the main spring(s)).

A supplementary spring of the constant-force springs may be extended from an inoperative (retracted/storage) configuration by pulling a handle attached to a leading end of the supplementary spring. A leading section of the supplementary spring may be extended until the supplementary spring can be placed in a coupled configuration.

The supplementary spring may be placed in the coupled configuration, while extended, such that the base tractive force applied to the limb is increased by a supplementary tractive force applied by the supplementary spring. The supplementary spring may be placed in the coupled configuration while the limb remains in traction. For example, the supplementary spring may be placed in the coupled configuration while the main springs continuously apply a base tractive force to the limb, without repositioning the limb, without repositioning the main springs (i.e., without extending or retracting the main springs, with the exception of any small change in main spring position produced by addition of the supplementary tractive force on the limb (e.g., due to limb stretching or slippage)), or any combination thereof.

The supplementary spring also may be placed back into an uncoupled configuration from the coupled configuration such that only the base tractive force is applied to the limb. Uncoupling may be performed while the main springs continuously apply a base tractive force to the limb, without repositioning the limb, without repositioning the main springs, or any combination thereof.

Further aspects of methods of applying traction to a limb are described in U.S. Pat. No. 7,131,955, which is incorporated herein by reference.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A system for applying traction to a patient's limb, comprising:
an orthopedic traction apparatus that attaches to a patient's limb, the traction apparatus including a plurality of constant-force springs supported rotatably by the traction apparatus such that each spring is extendable by unwinding, the plurality of constant-force springs including one or more main springs operatively disposed to apply a base tractive force to the limb,
wherein the plurality of constant-force springs also includes at least one supplementary spring that is changeable between an uncoupled configuration that does not apply a supplementary tractive force to the limb and a coupled configuration that applies the supplementary tractive force to the limb, and wherein the at least one supplementary spring is changeable reversibly between the uncoupled and coupled configurations while the base tractive force is applied continuously to the limb and without repositioning the limb, thereby providing discrete adjustment of traction force while the limb remains in traction.

2. The system of claim 1, wherein a leading end of the at least one supplementary spring is connected to a handle and to at least a portion of a fastener mechanism, and wherein the handle is configured to be manipulated to extend the supplementary spring and to actuate the fastener mechanism such that the supplementary spring is placed in the coupled configuration.

3. The system of claim 1, wherein at least two of the constant-force springs unwind by rotation about respective axes that are transverse to each other.

4. The system of claim 2, wherein the plurality of constant-force springs includes a first pair of springs arranged transversely to a second pair of springs.

5. The system of claim 1, wherein all of the constant-force springs rotate about axes that are parallel to one another.

6. The system of claim 1, wherein the orthopedic traction apparatus includes a frame and a carriage assembly that is movable with respect to the frame, wherein the one or more main springs couple the frame to the carriage assembly to apply the base tractive force, and wherein the at least one supplementary spring couples the frame to the carriage assembly in the coupled configuration but not in the uncoupled configuration.

7. The system of claim 6, wherein the frame includes a base configured to receive a first region of the limb and a bridge component having opposing ends, and wherein the bridge component is pivotably coupled to the base at one of the opposing ends and is coupled to the carriage assembly by the one or more main springs at the other opposing end.

8. The system of claim 6, wherein each of the constant-force springs is supported by the frame whether or not the at least one supplementary spring is in the uncoupled configuration or the coupled configuration.

9. The system of claim 6, wherein a leading end of each main spring is attached to the frame or to at least a portion of the carriage assembly more permanently than a leading end of the at least one supplementary spring in the coupled configuration.

10. The system of claim 1, wherein the one or more main springs apply a relatively larger tractive force, and wherein the at least one supplementary spring includes at least two supplementary springs that each apply a relatively smaller tractive force.

11. An apparatus for applying traction to a patient's limb, comprising:
- a base that receives a proximal region of the patient's limb;
- a spanning member connected to the base and configured to apply tractive forces to a distal region of the patient's limb, the spanning member including
  - a bridge component having a first end connected to the base and a second end disposed near the distal region of the patient's limb,
  - a plurality of constant-force springs connected rotatably to the second end of the bridge component such that each spring is extendable by unwinding, and
  - a carriage assembly including at least one securement member that engages the distal region of the patient's limb, the carriage assembly being coupled movably to the second end of the bridge component by one or more main springs of the constant-force springs such that a base tractive force is applied to the distal region of the patient's limb over a continuous range of separation of the second end of the bridge component and the carriage assembly,
- wherein the plurality of constant-force springs also includes at least one supplementary spring, wherein a leading end of the at least one supplementary spring is connected to a handle and to at least a portion of a fastener mechanism, and wherein the handle is configured to be manipulated to extend the supplementary spring and to actuate the fastener mechanism such that the supplementary spring is attached to the carriage assembly and such that at least one supplementary tractive force is added reversibly to the base tractive force while the base tractive force is applied continuously to the limb and without repositioning the limb.

12. The apparatus of claim 11, wherein at least two of the constant-force springs unwind by rotation about respective axes that are transverse to each other.

13. The apparatus of claim 12, wherein the plurality of constant-force springs includes a first pair of springs arranged transversely to a second pair of springs.

14. The apparatus of claim 11, wherein the plurality of constant-force springs includes at least three springs disposed on at least three respective sides of an axis.

15. The apparatus of claim 11, wherein all of the constant-force springs rotate about axes that are parallel to one another.

16. A method of applying traction to a patient's limb using a traction apparatus including a plurality of constant-force springs supported rotatably by the traction apparatus such that each spring is extendable by unwinding, the constant-force springs including one or more main springs operatively disposed to apply a base tractive force to a limb and at least one supplementary spring that is changeable between an uncoupled configuration in which the supplementary spring is not operatively disposed to apply a supplementary tractive force to the limb and a coupled configuration in which the supplementary spring is operatively disposed to apply the supplementary tractive force, the method comprising:
- attaching the traction apparatus to a patient's limb;
- extending the supplementary spring independently of the one or more main springs by pulling a handle attached to a leading end of the supplementary spring;
- placing the supplementary spring in the coupled configuration from the uncoupled configuration while extended; and
- applying the base tractive force and the supplementary tractive force together to the limb.

17. The method of claim 16, further comprising a step of uncoupling the supplementary spring such that only the base tractive force is applied to the limb, and wherein the step of uncoupling is performed without repositioning the limb.

18. The method of claim 16, further comprising a step of performing surgery on the limb while the limb is under traction.

19. The method of claim 16, wherein the step of extending is performed while the one or more main springs apply the base tractive force to the patient's limb.

20. The method of claim 16, wherein the supplementary spring is a first supplementary spring that applies a first supplementary tractive force, and wherein the plurality of constant-force springs includes a second supplementary spring that applies a second supplementary tractive force, further comprising repeating the steps of extending and placing using the second supplementary spring such that the base tractive force is applied to the limb together with both the first and second supplementary tractive forces.

* * * * *